US00PP25002P2

(12) United States Plant Patent
Jones

(10) Patent No.: US PP25,002 P2
(45) Date of Patent: Oct. 21, 2014

(54) ***NEMESIA* PLANT NAMED 'SUNJONBUSP'**

(50) Latin Name: ***Nemesia denticulata*×*Nemesia caerulea***
Varietal Denomination: Sunjonbusp

(71) Applicant: Jimmy Jones, Netherwent (GB)

(72) Inventor: Jimmy Jones, Netherwent (GB)

(73) Assignee: Suntory Flowers Ltd., Tokyo (JP)

( * ) Notice: Subject to any disclaimer, the term of this patent is extended or adjusted under 35 U.S.C. 154(b) by 128 days.

(21) Appl. No.: 13/694,148

(22) Filed: Oct. 31, 2012

(51) Int. Cl.
*A01H 5/00* (2006.01)

(52) U.S. Cl.
USPC ..... Plt./458

(58) Field of Classification Search
USPC ..... Plt./458
See application file for complete search history.

*Primary Examiner* — Susan McCormick Ewoldt
(74) *Attorney, Agent, or Firm* — C. A. Whealy

(57) ABSTRACT

A new and distinct cultivar of *Nemesia* plant named 'Sunjonbusp', characterized by its compact and upright growth habit; freely branching habit; freely flowering habit; long flowering period; fragrant violet, light red purple and white-colored flowers; and good garden performance.

1 Drawing Sheet

Botanical designation: *Nemesia denticulata*×*Nemesia caerulea.*

Cultivar denomination: 'SUNJONBUSP'.

BACKGROUND OF THE INVENTION

The present invention relates to a new and distinct cultivar of *Nemesia* plant, botanically known as *Nemesia denticulata*×*Nemesia caerulea* and hereinafter referred to by the name 'Sunjonbusp'.

The new *Nemesia* plant is a product of a planned breeding program conducted by the Inventor in St. Brides Netherwent, Monmouthshire, Wales. The objective of the breeding program is to create new compact and freely-branching *Nemesia* plants with unique and attractive flower coloration.

The new *Nemesia* plant originated from a cross-pollination made by the Inventor on Apr. 10, 2006 in St. Brides Netherwent, Monmouthshire, Wales of a proprietary selection of *Nemesia denticulata*×*Nemesia caerulea* identified as code number 6N231, not patented, as the female, or seed, parent with a proprietary selection of *Nemesia denticulata*×*Nemesia caerulea* identified as code number 6N93, not patented, as the male, or pollen, parent. The new *Nemesia* plant was discovered and selected by the Inventor as a single flowering plant within the progeny of the stated cross-pollination in a controlled greenhouse environment in St. Brides Netherwent, Monmouthshire, Wales on Jul. 20, 2006.

Asexual reproduction of the new *Nemesia* plant by vegetative cuttings in a controlled environment in St. Brides Netherwent, Monmouthshire, Wales since Jul. 20, 2006 has shown that the unique features of this new *Nemesia* plant are stable and reproduced true to type in successive generations.

SUMMARY OF THE INVENTION

Plants of the new *Nemesia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunjonbusp'. These characteristics in combination distinguish 'Sunjonbusp' as a new and distinct *Nemesia* plant:

1. Compact and upright growth habit.
2. Freely branching habit.
3. Freely flowering habit.
4. Long flowering period.
5. Fragrant violet, light red purple and white-colored flowers.
6. Good garden performance.

Plants of the new *Nemesia* can be compared to plants of the female parent selection. Plants of the new *Nemesia* differ primarily from plants of the female parent selection in flower color as plants of the female parent selection have light blue and white-colored flowers.

Plants of the new *Nemesia* can be compared to plants of the male paren selection. Plants of the new *Nemesia* differ primarily from plants of the male parent selection in flower color as plants of the male parent selection have white-colored flowers. In addition, plants of the new *Nemesia* are shorter than plants of the male parent selection.

Plants of the new *Nemesia* can also be compared to plants of *Nemesia denticulata*×*Nemesia caerulea* 'Sunjonpiho', disclosed in U.S. Plant Pat. No. 22,841. In side-by-side comparisons, plants of the new *Nemesia* differed from plants of 'Sunjonpiho' in the following characteristics:

1. Plants of the new *Nemesia* were more compact than plants of 'Sunjonpiho'.
2. Plants of the new *Nemesia* had thicker lateral branches with longer internodes than plants of 'Sunjonpiho'.
3. Plants of the new *Nemesia* had shorter upper petals than plants of 'Sunjonpiho'.
4. Flowers of plants of the new *Nemesia* were fragrant whereas flowers of plants of 'Sunjonpiho' were not fragrant.
5. Plants of the new *Nemesia* and 'Sunjonpiho' differed in flower color as plants of 'Sunjonpiho' purple violet, red purple and white-colored flowers.

6. Plants of the new *Nemesia* had longer peduncles than plants of 'Sunjonpiho'.

BRIEF DESCRIPTION OF THE PHOTOGRAPHS

The accompanying colored photographs illustrate the overall appearance of the new *Nemesia* plant showing the colors as true as it is reasonably possible to obtain in colored reproductions of this type. Colors in the photographs may differ slightly from the color values cited in the detailed botanical description which accurately describe the colors of the new *Nemesia* plant.

The photograph at the top of the sheet comprises a side perspective view of a typical flowering plant of 'Sunjonbusp' grown in a container.

The photograph at the bottom of the sheet is a close-up view of typical flowers of 'Sunjonbusp'.

DETAILED BOTANICAL DESCRIPTION

The aforementioned photographs and following observations, measurements and values describe plants grown during the late spring in 15-cm containers in an outdoor nursery in Higashiomi, Shiga, Japan and under commercial cultural practices. During the production of the plants, day temperatures averaged 15° C. and night temperatures averaged 5° C. Plants were pinched one time and were four months old when the photographs and description were taken. In the following description, color references are made to The Royal Horticultural Society Colour Chart, 2007 Edition, except where general terms of ordinary dictionary significance are used.

Botanical classification: *Nemesia denticulata*×*Nemesia caerulea* 'Sunjonbusp'.

Parentage:

*Female, or seed, parent*.—Proprietary selection of *Nemesia denticulata*×*Nemesia caerulea* identified as code number 6N231, not patented.

*Male, or pollen, parent*.—Proprietary selection of *Nemesia Denticulata*×*Nemesia caerulea* identified as code number 6N93, not patented.

Propagation:

*Type*.—By vegetative cuttings.

*Time to initiate roots, summer*.—About two weeks at temperatures of about 18° C.

*Time to initiate roots, winter*.—About 18 days at temperatures of about 18° C.

*Time to produce a rooted young plant, summer and winter*.—About three weeks at temperatures of about 18° C.

*Root description*.—Fibrous; white in color.

*Rooting habit*.—Moderately freely branching; medium density.

Plant description:

*Plant and growth habit*.—Compact and upright growth habit; freely branching with two lateral branches potentially forming at every node; vigorous growth habit.

*Plant height*.—About 18.5 cm.

*Plant diameter*.—About 24.3 cm.

Lateral branch description:

*Length*.—About 19.9 cm.

*Diameter*.—About 2.4 mm.

*Internode length*.—About 3 cm.

*Aspect*.—Mostly upright.

*Texture*.—Smooth, glabrous.

*Color*.—Close to 144A.

Foliage description:

*Arrangement*.—Opposite, simple.

*Length*.—About 3.5 cm.

*Width*.—About 1.5 cm.

*Shape*.—Lanceolate.

*Apex*.—Acute.

*Base*.—Truncate.

*Margin*.—Shallowly serrate.

*Texture, upper and lower surfaces*.—Smooth, glabrous.

*Venation pattern*.—Pinnate, reticulate.

*Color*.—Developing leaves, upper surface: Close to 137B. Developing leaves, lower surface: Close to 138B. Fully expanded leaves, upper surface: Close to N137C; venation, close to 138B. Fully expanded leaves, lower surface: Close to N137C; venation, close to N137C.

*Petioles*.—Length: About 2.9 mm.

*Diameter*.—About 2.4 mm.

*Texture, upper and lower surfaces*.—Smooth, glabrous.

*Color, upper and lower surfaces*.—Close to 143C.

Flower description:

*Flower arrangement and flowering habit*.—Bilabiate solitary flowers arranged on terminal racemes; flowering acropetally towards the apex; flowers facing mostly outwardly; freely flowering habit with about five flowers per raceme and about 26 racemes developing per plant.

*Fragrance*.—Fragrant, pleasant.

*Natural flowering season*.—In Japan, plants flower naturally from early spring to early summer; flowering continuous during this period; early flowering habit, flowers begin flowering about three months after planting.

*Flower longevity*.—Flowers last about five to seven days on the plant; flowers not persistent.

*Flower size* (*diameter by length*).—About 2 cm by 2.2 cm.

*Flower depth*.—About 1.1 cm.

*Flower buds*.—Length: About 7.7 mm. Diameter: About 6.5 mm. Shape: Obovate. Color: Close to 77C.

*Petals*.—Arrangement: Five modified petals; four upper petals fused at the base forming an upright lobed and arched banner lip; lower petal modified into a larger lip with a convex oval protuberance serving as a nectar guide and insect landing platform. Shape, upper lip: Elliptic. Shape, lower lip: Reniform. Apex, upper lip: Rounded. Apex, lower lip: Obcordate. Margin, upper lip: Entire; undulate. Margin, lower lip: Entire; slightly undulate. Length, upper lip: About 10.8 mm. Length, lower lip: About 12.3 mm. Width, upper lip: About 5.3 mm to 17.7 mm. Width, lower lip: About 14.2 mm. Nectar guide length: About 4.4 mm. Nectar guide width: About 3.6 mm. Texture, upper and lower lips, upper and lower surfaces: Smooth, glabrous. Color, upper lip: When opening, upper surface: Close to 73B overlain with close to 86A; center, close to 1C. When opening, lower surface: Close to N87B. Fully opened, upper surface: Close to 73C overlain with close to 86B; center, close to 1C. Fully opened, lower surface: Close to 86D. Color, lower lip: When opening, upper surface: Close to NN155C overlain with close to 71D; nectar guide, close to 6A. When opening, lower surface: Close to 76A; towards the margins, close to 75B. Fully opened, upper surface: Close to NN155C overlain with close to 71D; nectar guide, close to 6A; color does not fade with development. Fully opened, lower surface: Close to 84A; towards the margins, close to 75B.

*Tube*.—Length: About 3.6 mm. Diameter: About 4.5 mm. Color: Close to 1C.

*Spur*.—Length: About 8.3 mm. Diameter: About 0.8 mm. Color: Close to 176BB.

*Sepals*.—Arrangement: Calyx star-shaped with five sepals in a single whorl and fused at the base. Length: About 2.1 mm. Width: About 1.4 mm. Shape: Lanceolate. Apex: Acute. Margin: Entire. Texture, upper and lower surfaces: Smooth, glabrous. Color, upper surface: Close to 137C. Color, lower surface: Close to 137D.

*Peduncles*.—Length: About 8.6 cm. Diameter: About 1.2 mm. Strength: Moderately strong; flexible. Texture: Pubescent. Color: Close to 144B.

*Pedicels*.—Length: About 10.9 mm. Diameter: About 0.4 mm. Strength: Moderately strong; flexible. Texture: Smooth, glabrous. Color: Close to 144B.

*Reproductive organs*.—Stamens: Quantity and arrangement: Four per flower. Stamen length: About 0.9 mm to 2.3 mm. Anther shape: Narrowly elliptic. Anther size: About 1.4 mm by 0.8 mm. Anther color: Close to 6C. Pollen amount: Moderate. Pollen color: Close to 6A. Pistils: Quantity: One per flower. Pistil length: About 2 mm. Style color: Close to 145C. Stigma shape: Ovate. Stigma color: Close to 145A. Ovary color: Close to 145A.

*Seeds and fruits*.—Seed and fruit development have not been observed on plants of the new *Nemesia*.

Pathogen & pest resistance: Plants of the new *Nemesia* have not been observed to be resistant to pests and pathogens common to *Nemesia* plants.

Garden performance: Plants of the new *Nemesia* have been observed have good garden performance and to tolerate wind, rain and temperatures ranging from 5° C. to 35° C.

It is claimed:

1. A new and distinct *Nemesia* plant named 'Sunjonbusp' as illustrated and described.

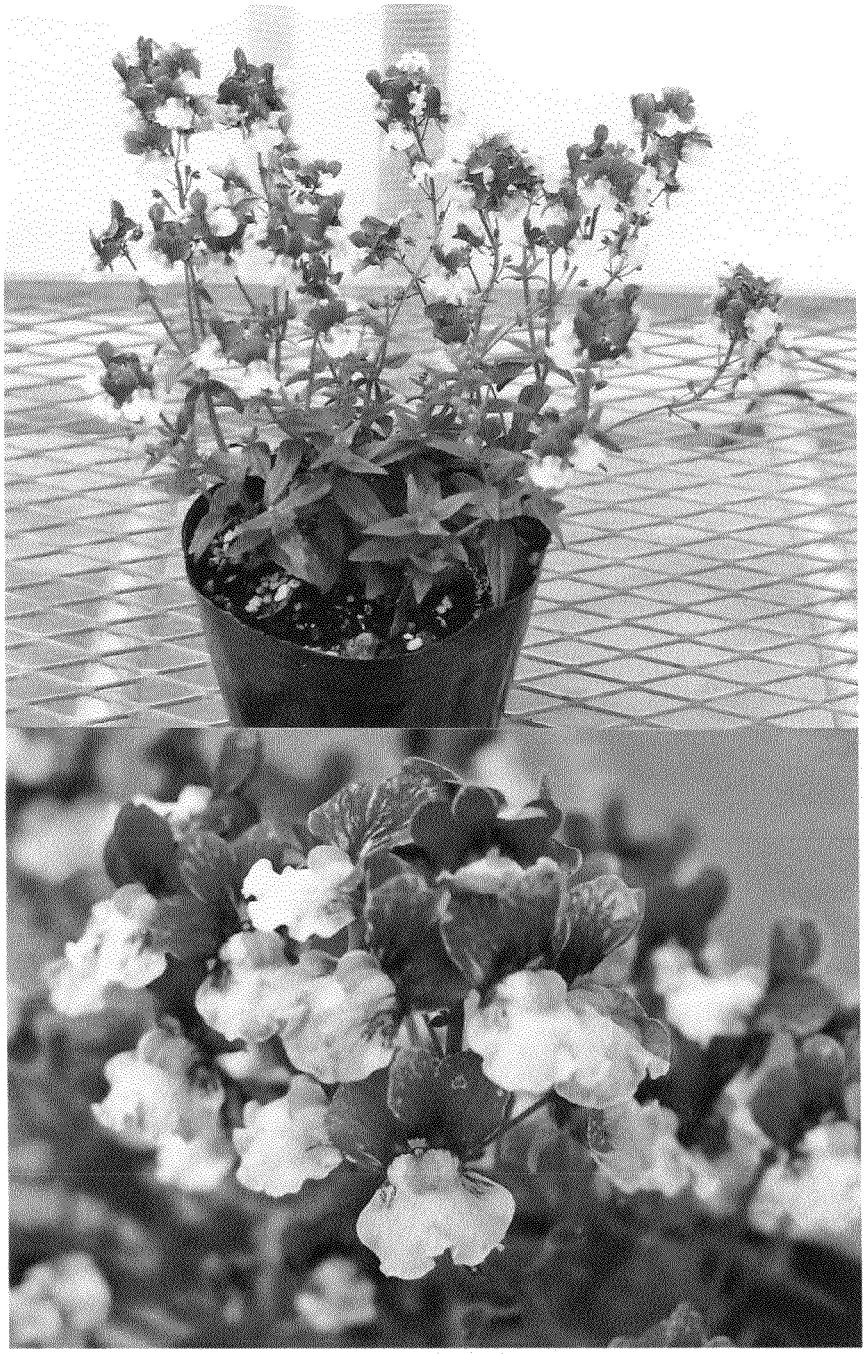

* * * * *